United States Patent [19]

Rizkalla

[11] Patent Number: 4,483,804

[45] Date of Patent: Nov. 20, 1984

[54] PREPARATION OF CARBOXYLIC ACID ANHYDRIDES

[75] Inventor: Nabil Rizkalla, River Vale, N.J.

[73] Assignee: The Halcon SD Group, Inc., New York, N.Y.

[21] Appl. No.: 430,095

[22] Filed: Sep. 30, 1982

[51] Int. Cl.³ ............................................. C07C 51/12
[52] U.S. Cl. ..................................................... 260/546
[58] Field of Search ........................................ 260/546

[56] References Cited

U.S. PATENT DOCUMENTS 4,335,059  6/1982  Rizkalla ................................ 260/546

Primary Examiner—James H. Reamer
Assistant Examiner—L. Hendriksen
Attorney, Agent, or Firm—William C. Long; Riggs T. Stewart; Harold N. Wells

[57] ABSTRACT

A carboxylic acid anhydride, such as acetic anhydride, is prepared from a carboxylate ester or a hydrocarbyl ether in carbonylation processes comprising the use of an iodide or bromide carbon monoxide and a molybdenum-nickel-alkali metal or a tungsten-nickel-alkali metal catalyst.

4 Claims, No Drawings

PREPARATION OF CARBOXYLIC ACID ANHYDRIDES

This invention relates to the preparation of anhydrides of carboxylic acids, more particularly mono-carboxylic acids, and especially the anhydrides of lower alkanoic acids, such as acetic anhydride, by carbonylation.

Acetic anhydride has been known as an industrial chemical for many years and large amounts are used in the manufacture of cellulose acetate. It has commonly been produced on an industrial scale by the reaction of ketene and acetic acid. It is also known that acetic anhydride can be produced by the decomposition of ethylidene diacetate, as well as by the oxidation of acetaldehyde, for example. Each of these "classic" processes has well-known drawbacks and disadvantages and the search for an improved process for the production of acetic anhydride has been a continuing one. Proposals for producing anhydrides by the action of carbon monoxide upon various reactants (carbonylation) have been described, for example, in Reppe et al U.S. Pat. Nos. 2,729,561; 2,730,546; and 2,789,137. However, such prior proposals involving cobalt or nickel catalysts have required the use of very high pressures. In later patents, carbonylation at lower pressures has been proposed but only as a route to the preparation of acetic acid. French Pat. No. 1,573,130, for example, describes the carbonylation of methanol and mixtures of methanol with methyl acetate in the presence of compounds of Group VIII noble metals such as iridium, platinum, palladium, osmium, and ruthenium and in the presence of bromine or iodine under more moderate pressures than those contemplated by Reppe et al. Similarly, South African Pat. No. 68/2174 produces acetic acid from the same reactants using a rhodium component with bromine or iodine. Schultz (U.S. Pat. Nos. 3,689,533 and 3,717,670) has disclosed a vapor-phase process for acetic acid production employing various catalysts comprising a rhodium component dispersed on a carrier. None of these later carbonylation disclosures, however, refers to or contemplates the preparation of acetic anhydride or other carboxylic acid anhydrides.

More recently, improved processes for preparing carboxylic acid anhydrides, including acetic anhydride, have been disclosed in British Pat. No. 1,468,940 and in U.S. Pat. No. 4,115,444. In these processes, however, a Group VIII noble metal is an essential catalyst component. Consequently, while entirely effective and operable at pressures lower than those previously required for anhydride manufacture, these processes necessitate the use of expensive, relatively rare metals.

U.S. Pat. No. 4,002,678 discloses the use of a non-noble metal system for anhydride manufacture involving a promoted nickel-chromium catalyst and U.S. Pat. No. 4,335,059 discloses a related process which effects the carbonylation of a carboxylate ester and/or a hydrocarbyl ether to produce carboxylic acid anhydrides by using a molybdenum-nickel or tungsten-nickel catalyst and a promoter comprising an organo-phosphorus or an organo-nitrogen compound. European published application No. 0 048 210 shows the carbonylation of esters to produce anhydrides by the use of a nickel catalyst, an alkyl or acyl iodide, a sulfone solvent, and an alkali metal salt, an alkaline earth metal salt, a quaternary ammonium iodide, or a quaternary phosphonium iodide. European published application No. 0 050 084 shows a related process using a nickel catalyst, an alkyl or acyl iodide, a carboxylic acid amide solvent, and an alkali metal or an alkaline earth metal salt. These several processes involving nickel catalysts make possible carbonylation at modest pressures without requiring the use of a noble metal catalyst but there is room for improvement in terms of reaction rate and productivity without need for organic promoters.

It is an object of the present invention to provide an improved process for the manufacture of carboxylic acid anhydrides, especially lower alkanoic anhydrides, such as acetic anhydride, which requires neither high pressures nor Group VIII noble metals nor organic promoters.

In accordance with the invention, carbonylation of a carboxylic ester and/or a hydrocarbyl ether is carried out by using a molybdenum-nickel-alkali metal or a tungsten-nickel-alkali metal co-catalyst and in the presence of an iodide. The surprising discovery has been made that this co-catalyst system in an environment of the character indicated makes possible carbonylation of esters and ethers not only at relatively low pressures but with rapid, high yield production of carboxylic acid anhydrides. The iodide can be replaced with a bromide.

The outstanding effectiveness of the catalyst system of the process of this invention is particularly surprising in view of the experimental data reported in European published application No. 0 035 458 which shows the carbonylation of methanol to produce acetic acid in the presence of a nickel catalyst, an alkyl halide, an alkali or alkaline earth halide, and a solvent which is a tetramethylenesulfone or its derivative or an alkyl ether of a polyethylene glycol or an amide. In that publication, experiments using nickel in combination with molybdenum or tungsten showed absolutely no reaction even after two hours. It has also been observed that when nickel-based catalysts are ordinarily used in carbonylation reactions, there is a tendency for the nickel component to be volatilized and to appear in the vapors from the reaction. It has been surprisingly observed that, with the catalyst system of this invention, the volatility of the nickel is strongly suppressed and a highly-stable catalyst combination results.

Thus, in accordance with the invention, carbon monoxide is reacted with a carboxylate ester, especially a lower alkyl alkanoate, or a hydrocarbyl ether such as a lower alkyl ether, to produce a carboxylic anhydride, such as a lower alkanoic anhydride, the carbonylation taking place in the presence of an iodide, e.g., a hydrocarbyl iodide, especially a lower alkyl iodide, such as methyl iodide. Thus, acetic anhydride, for example, can be effectively prepared in a representative case by subjecting methyl acetate or dimethyl ether to carbonylation in the presence of methyl iodide. In all cases, the carbonylation is carried out under anhydrous conditions in the presence of the co-catalyst system described above. Moreover, an ester-ether mixture can be carbonylated if desired.

In like manner, other lower alkanoic anhydrides, i.e., anhydrides of lower alkanoic acids, such as propionic anhydride, butyric anhydrides, and valeric anhydrides, can be produced by carbonylating the corresponding lower alkyl alkanoate or a lower alkyl ether. Similarly, other carboxylic acid anhydrides, e.g., the anhydrides of other alkanoic acids, such as those containing up to 12 carbon atoms, for example, capric anhydrides, caprylic anhydrides and lauric anhydrides, and like higher anhydrides are produced by carbonylating the corresponding ester, e.g., alkyl alkanoates containing up to 11 carbon atoms in the alkyl group and up to 12 carbon atoms in the carboxylate group, or aryl esters, or the corresponding ether, such as heptyl caprylate, nonyl decanoate, undecyl laurate, phenyl benzoate, heptyl ether, nonyl ether, phenyl ether, and the like.

It is preferred that the reactants be selected so that the resulting anhydride will be a symmetrical anhydride, i.e., having two identical acyl groups, viz., wherein R in equations (1) and (2) is the same in each instance, but it is within the scope of the invention to produce non-symmetrical or mixed anhydrides, and this can be readily effected by using different combinations of reactants, e.g., by using compounds having different R groups in the foregoing reactions, as will be obvious to persons skilled in the art.

The above-described reactions can be expressed as follows:

$$CO + RCOOR \rightarrow (RCO)_2O \quad (1)$$

$$2CO + ROR \rightarrow (RCO)_2O \quad (2)$$

wherein R is a hydrocarbyl radical which may be saturated, e.g., alkyl of 1 to 11 carbon atoms, or monocyclic aryl, e.g., phenyl or aralkyl, e.g., benzyl. Preferably, R is lower alkyl, i.e., an alkyl group of 1 to 4 carbon atoms, such as methyl, ethyl, n-propyl, i-propyl, n-butyl, sec-butyl and t-butyl.

The hydrocarbyl radical may be substituted with substituents which are inert in the reactions of the invention.

The more volatile components such as alkyl iodide and unreacted ether or ester in the final product mixture can be readily removed, as by distillation, for recycling, and the net yield of product is substantially exclusively the desired carboxylic anhydride. In the case of liquid-phase reaction which is preferred, the organic compounds are easily separated from the metal-containing components, as by distillation. The reaction is suitably carried out in a reaction zone to which the carbon monoxide, the ester or ether, the iodide, and the specified co-catalyst are fed. No water is produced in the above-described reactions and anhydrous or substantially anhydrous conditions are employed.

In carrying out the process of the invention, a wide range of temperatures, e.g., 150° to 250° C. are suitable but temperatures above 180° up to 250° C. are preferably used and the more preferred temperatures generally lie in the range of 200° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but, as previously mentioned, it is a feature of the invention that excessively high pressures, which require special high-pressure equipment, are not necessary. In general, the reaction is effectively carried out by employing a carbon monoxide partial pressure which is preferably 15 to under 2000 psi and most preferably 30 to 500 psi, although carbon monoxide partial pressures of 1 to 5,000 psi or even 10,000 can also be employed. By establishing the partial pressure of carbon monoxide at the values specified, adequate amounts of this reactant are always present. The total pressure is, of course, that which will provide the desired carbon monoxide partial pressure and preferably it is that required to maintain the liquid phase and in this case the reaction can be advantageously carried out in an autoclave or similar apparatus. The final reaction mixture will normally contain volatile components such as a hydrocarbyl iodide, unreacted ester or ether along with the product anhydride and these volatile components, after separation from the anhydride, can be recycled to the reaction. At the end of the desired residence time the reaction mixture is separated into its several constituents, as by distillation. Preferably, the reaction product is introduced into a distillation zone which may be a fractional distillation column, or a series of columns, effective to separate the volatile components from the product anhydride and to separate the product anhydride from the less volatile catalyst components of the reaction mixture. The boiling points of the volatile components are sufficiently far apart that their separation by conventional distillation presents no particular problem. Likewise, the higher boiling organic components can be readily distilled away from the metal co-catalyst components and any organic promoter which may be in the form of a relatively non-volatile complex. The co-catalyst components can then be combined with fresh amounts of ester or ether and carbon monoxide and reacted to produce additional quantities of anhydride.

The process is advantageously carried out in the presence of a solvent or diluent, particularly when the reactant has a relatively low boiling point, as in the case of dimethyl ether. The presence of a higher boiling solvent or diluent, which may be the product anhydride itself, e.g., acetic anhydride in the case of dimethyl ether, or which may be the corresponding ester, e.g., methyl acetate, again in the case of methyl ether, will make it possible to employ more moderate total pressure. Alternatively, the solvent or diluent may be any organic solvent which is inert in the environment of the process such as hydrocarbons, e.g., octane, benzene, toluene, or carboxylic acids, e.g., acetic acid, and the like. The carboxylic acid, when used, should preferably correspond to the anhydride being produced. A solvent or diluent is suitably selected which has a boiling point sufficiently different from the desired product in the reaction mixture so that it can be readily separated, as will be apparent to persons skilled in the art.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like other reactants should, however, be essentially dry, i.e., the CO and the other reactants should be reasonably free from water. The presence of minor amounts of water such as may be found in the commercial forms of the reactants is, however, entirely acceptable. Hydrogen which may be present as an impurity is not objectionable and even may tend to stabilize the catalyst. Indeed, in order to obtain low CO partial pressures the CO fed may be diluted with hydrogen or any inert gas such as those above mentioned. Such diluents can be used in amounts up to 95%.

The co-catalyst components can be employed in any convenient form. For example, the nickel and the molybdenum or tungsten can be the metals themselves in finely-divided form, or a compound, both organic or inorganic, which is effective to introduce these co-catalyst components into the reaction system. Thus, typical compounds include the carbonate, oxide, hydroxide, bromide, iodide, chloride, oxyhalide, hydride, lower alkoxide (methoxide) phenoxide, or Mo, W or Ni carboxylates wherein the carboxylate ion is derived from an alkanoic acid of 1 to 20 carbon atoms such as acetates, butyrates, decanoates, laurates, benzoates, and the like. Similarly, complexes of these co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl. Particularly preferred are the elemental forms, compounds which are halides, especially iodides, and organic salts, e.g., salts of the monocarboxylic acid corresponding to the acid being produced.

The alkali metal component, e.g., a metal of Group IA of the Periodic Table such as lithium, potassium, sodium, and cesium, is suitably employed as a compound, especially a salt, and most preferably a halide, e.g., an iodide. The preferred alkali metal is lithium. The alkali metal component can, however, also be employed as the hydroxide, carboxylate, alkoxide or in the form of other convenient compounds such as are referred to above in connection with the other co-catalyst components, and typical alkali metal components are illustrated by sodium iodide, potassium iodide, cesium iodide, lithium iodide, lithium bromide, lithium chloride, lithium acetate, and lithium hydroxide.

It will be understood that the above-mentioned compounds and complexes are merely illustrative of suitable forms of the several co-catalyst components and are not intended to be limiting.

The specified co-catalyst components employed may contain impurities normally associated with the commercially available metal or metal compounds and need not be purified further.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 millimol to 1 mol per liter or reaction mixture, preferably 15 millimoles to 500 millimoles per liter and most preferably 15 millimoles to 150 millimoles per liter.

The ratio of nickel to the molybdenum, or tungsten co-catalyst component can vary. Typically, it is one mol of the nickel component per 0.01 to 100 mols of the second co-catalyst component, i.e., the molybdenum, or tungsten, component, preferably the nickel component is used in the amount of 1 mol per 0.1 to 20 mols, most preferably 1 mol per 1 to 10 mols of the second co-catalyst component. Similarly, the ratio of nickel to the alkali metal component can vary, e.g., one mole of nickel per 1 to 1000 mols of alkali metal component, preferably 10 to 100 and most preferably 20 to 50.

The amount of iodide component may also vary widely but, in general, it should be present in an amount of at least 0.1 mol (expressed as I) per mol of nickel. Typically, there are used 1 to 100 mols of the iodide per mol of nickel, preferably 2 to 50 mols per mol. Ordinarily, more than 200 mols of iodide per mol of nickel are not used. It will be understood, however, that the iodide component does not have to be added to the system as a hydrocarbyl iodide but may be supplied as another organic iodide or as the hydroiodide or other inorganic iodide, e.g., a salt, such as the alkali metal or other metal salt, or even as elemental iodine. The foregoing also applies to a bromide component when the iodide is replaced with a bromide.

As previously mentioned, the catalyst system of this invention comprises an iodide component and a molybdenum-nickel-alkali metal or tungsten-nickel-alkali metal co-catalyst component. The catalyst system of this invention permits the production of carboxylic acids in high yields in short reaction times without the use of Group VIII noble metals and the presence of the alkali metal component together with the molybdenum or tungsten component makes possible good results with relatively small amounts of co-catalyst components and reduced quantities of nickel in comparison with prior art processes involving a nickel-containing catalyst.

A particular embodiment of the catalyst comprising the molybdenum-nickel-alkali metal or tungsten-nickel-alkali metal co-catalyst component and the iodide component can be represented by the following formula: X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is an iodide source which is hydrogen iodide, iodine, an alkyl iodide wherein the alkyl group contains 1 to 20 carbon atoms or an alkali metal iodide, and Q is the alkali metal component. The preferred alkali metal is lithium as previously indicated, and being in the form of an iodide or a bromide or a carboxylate as defined for X and T, the molar ratio of X to T being 0.1-10:1, the molar ratio of X+T to Q being 0.1-10:1, and the molar ratio of Z to X+T being 0.01-0.1:1. The iodide component can be replaced with a bromide.

It will be apparent that the above-described reaction lends itself readily to continuous operation in which the reactants and catalyst are continuously supplied to the appropriate reaction zone and the reaction mixture cntinuously distilled to separate the volatile organic constituents and to provide a net product consisting essentially of carboxylic acid with the other organic components being recycled and, in a liquid-phase reaction a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most preferably 175° to 255° C., a pressure of 1 to 5,000 p.s.i.a., preferably 59 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention. In the examples, all parts are by weight and percentages are on a molar basis, unless otherwise indicated.

EXAMPLE 1

A one-liter Parr autoclave was charged with 250.4 parts of methyl acetate, 190.1 parts of methyl iodide, 120 parts of acetic acid as solvent, 7.5 parts of nickel iodide, 15.3 parts of molybdenum carbonyl, and 60.2 parts of lithium iodide. The reactor was flushed for 5 minutes with a 95%/5% mixture of carbon monoxide and hydrogen and then pressured with this gas mixture to 604 psig. Then the reactor was heated to 195° C. and maintained at this temperature for 2 hours and 5 minutes, during which time the pressure was maintained at 1187 psig by continuously introducing the 95%/5% gas mixture. The contents of the reactor were then removed and analyzed by gas chromatography. Analysis showed the reaction mixture to contain 32.1 wt. % of acetic anhydride, the remainder being methyl iodide, unreacted methyl acetate, acetic acid solvent and the catalyst components. This reaction produced acetic anhydride with a yield based on methyl acetate of 66.9% at a rate of 12.3 mol per liter per hour.

EXAMPLE 2

The autoclave described in Example 1 was charged with 250.3 parts of methyl acetate, 190.5 parts of methyl iodide, 120 parts of acetic acid as solvent, 7.5 parts of nickel iodide, 15.1 parts of molybdenum carbonyl, and 60.1 parts of lithium iodide. The procedure described in Example 1 was followed at a temperature of 200° C. and a pressure of 1216 psig for 2 hours. G.C. analysis showed the reaction mixture to contain 31.74 wt. % of acetic anhydride, the remainder being as in Example 1. This reaction produced acetic anhydride with a yield based on methyl acetate of 67% at the rate of 3.5 mols per liter per hour.

EXAMPLE 3

The autoclave of Example 1 was charged with 200.4 parts of methyl acetate, 200.1 parts of methyl iodide, 150.5 parts of acetic acid as solvent, 10 parts of nickel iodide, 20.2 parts of molybdenum carbonyl, and 60 parts of lithium iodide. The procedure of Example 1 was followed at a temperature of 190° C. and a pressure of 1204 psig for 2 hours. G.C. analysis showed the reaction mixture to contain 23.24 wt. % of acetic anhydride, the remainder being as in Example 1. This reaction produced acetic anhydride with a yield based on methyl acetate of 54% at a rate of 3 mols per liter per hour.

EXAMPLE 4

The autoclave of Example 1 was charged with 200 parts of methyl acetate, 100 parts of methyl iodide, 50.1 parts of acetic acid as solvent, 7.5 parts of nickel iodide, 15 parts of molybdenum carbonyl, and 60 parts of lithium iodide. The reactor was flushed 3 times with 50 psig of carbon monoxide and then pressured to 500 psig with carbon monoxide. Then the reactor was heated to 200° C. and maintained at this temperature for 2 hours, during which time the pressure was maintained at 1050 psig by supplying carbon monoxide as required. G.C. analysis showed the reaction mixture to contain 33.4 wt. % of acetic anhydride, the remainder being as in Example 1. This reaction produced acetic anhydride with a yield based on methyl acetate of 47% at a rate of 2.14 mols per liter per hour.

EXAMPLE 5

The one-liter Parr autoclave was charged with 250 parts of methyl acetate, 190 parts of methyl iodide, 120 parts of acetic acid as solvent, 7.7 parts of nickel iodide, 15 parts of molybdenum carbonyl, and 60.1 parts of lithium iodide. The reactor was flushed 3 times with 50 psig of carbon monoxide and then pressured to 530 psig with carbon monoxide. Then the reactor was heated to 200° C. and maintained at this temperature for 1 hours and 16 minutes, during which time the pressure was maintained at 1200 psig by charging carbon monoxide as required. G.C. analysis showed the reaction mixture to contain 29.3 wt. % of acetic anhydride, the remainder being as in Example 1. This reaction produced acetic anhydride with a yield based on methyl acetate of 60% at a rate of 3.5 mols per liter per hour.

EXAMPLE 6

The autoclave of Example 1 was charged with 250 parts of methyl acetate, 100 parts of methyl iodide, 150.3 parts of acetic acid as solvent, 7.5 parts of nickel iodide, 15 parts of tungsten carbonyl, and 120 parts of lithium iodide. The procedure of Example 5 was followed for a reaction time of 1 hour. G.C. analysis showed the reaction mixture to contain 23.3 wt. % of acetic anhydride, the remainder being as in Example 1. This reaction produced acetic anhydride with a yield based on methyl acetate of 45% at a rate of 1.2 mols per liter per hour.

EXAMPLE 7

Example 4 was repeated but at 180° C. It was found that the yield and reaction rate fell to a considerable extent, indicating the need for a higher temperature to obtain the best results with the catalyst.

COMPARATIVE EXAMPLE

Example 4 was repeated except that the molybdenum carbonyl was omitted from the charge. The yield of acetic anhydride fell to 17% and the reaction rate to 0.79 mol per liter per hour.

What is claimed is:

1. A process for the preparation of carboxylic acid anhydrides which comprises reacting a carboxylate ester and/or a hydrocarbyl ether with carbon monoxide in the presence of a catalyst comprising a molybdenum-nickel-alkali metal or a tungsten-nickel-alkali metal co-catalyst component and in the presence of an iodide or bromide.

2. A process as defined in claim 1, wherein the co-catalyst component comprises molybdenum-nickel-alkali metal.

3. A process as defined in claim 1, wherein the alkali metal is lithium.

4. A process as defined in claim 3, wherein the co-catalyst comprises molybdenum-nickel-lithium.

* * * * *